United States Patent [19]

Urso

[11] Patent Number: 4,706,695

[45] Date of Patent: * Nov. 17, 1987

[54] INTERDENTAL CLEANING AND POLISHING TOOL

[76] Inventor: Charles L. Urso, 215 Newton St., Waltham, Mass. 02154

[*] Notice: The portion of the term of this patent subsequent to May 6, 2003 has been disclaimed.

[21] Appl. No.: 850,221

[22] Filed: Apr. 10, 1986

Related U.S. Application Data

[63] Continuation-in-part of Ser. No. 558,826, Dec. 7, 1983, Pat. No. 4,586,521.

[51] Int. Cl.$^4$ .............................................. A61C 15/00
[52] U.S. Cl. .................................................. 132/92 R
[58] Field of Search ................................. 132/92 R, 91

[56] References Cited

U.S. PATENT DOCUMENTS

| | | | |
|---|---|---|---|
| 2,467,221 | 4/1949 | Pastl | 132/92 R |
| 3,759,274 | 9/1973 | Warner | 132/92 R |
| 4,235,253 | 11/1980 | Moore | 132/92 R |
| 4,307,740 | 12/1981 | Florindez | 132/92 R |
| 4,458,702 | 7/1984 | Grollimund | 132/92 A |

Primary Examiner—Robert Peshock

[57] ABSTRACT

An interdental cleaning and polishing tool comprising a housing and a pair of tines pivotally supported on the housing wherein the tines receive teeth to be cleaned therebetween. Each tine having guides for guiding the transfer of dental floss from one tine to the other tine wherein the floss forms a movable span therebetween. A dispensing spool dispenses floss to one tine while a take-up spool retrieves floss from the other tine. Means are provided for oscillating the tines up and down relative to the teeth and for simultaneously producing continuous slow rotation of the take-up spool. Stationary shield tines individually enclose the oscillating tines to prevent the latter from contacting oral tissues. Means are provided for locking and unlocking the floss span so that when locked the span is immovably taut so that the same can be forced through tight spaces between adjacent teeth. Means are also provided to allow the span to yieldingly slacken if applied to oral tissues with greater than a predetermined amount of force, thereby protecting soft tissues. The tool is loaded with a covered floss dispensing spool which inhibits floss contamination. Used floss is level-wound on the take-up spool. The oral portion of the instrument is designed so that the shield tines, as well as the movable tines, can be cleaned by rinsing under hot running tap water without having to remove parts.

16 Claims, 5 Drawing Figures

INTERDENTAL CLEANING AND POLISHING TOOL

RELATED APPLICATION

This application is a continuation-in-part of a U.S. patent application, Ser. No. 558,826, filed Dec. 7, 1983 and now U.S. Pat. No. 4,586,521 issued May 6, 1986.

FIELD OF THE INVENTION

This invention relates to dental hygiene devices and specifically to powered devices for interdental cleaning.

BACKGROUND OF THE INVENTION

Cleaning the surfaces between adjacent teeth generally is a special problem. Such areas are not accessible to a tooth brush, yet they must be cleaned regularly. The consequence of not removing deposits there, especially on tooth surfaces within the gingival sulci, will very likely lead to diseases affecting teeth and periodontal tissues. The latter accounts for the large percentage of people who lose their natural teeth.

A cause of periodontal disease is initiated by bacteria acting on food particles deposited on tooth surfaces inside the gingival sulci. The deposits become plaque which later harden as a result of calcium deposition. As additional debris accumulate, a sequence of biological, physical, and biochemical events occur which eventually lead to destruction of previously healthy tissues.

A cleaning method supplementary to brushing is therefore necessary. Fairly good results have come from the use of dental floss held and manipulated with the hands. Floss tensioned within various types frames which are manipulated with the hands can also produce positive results. However, these techniques require skill with considerable perseverance and are in the main, arduous and burdensome tasks.

Efforts to reduce the interdental cleaning burden have produced some powered devices that are patented. A common problem with such devices, however, is that a segment of floss which becomes soiled during the cleaning process is returned to the target tissues with the return stroke of a reciprocating cycle. This is especially undesirable for people with gingivitis or periodontal disease since the soiled floss can pass repeatedly over or across inflamed or disease injured tissues. The cleaning action of most of the powered prior art devices reciprocates the floss in a transverse saw-like motion which is undesirable across soft tissues.

DISCLOSURE OF THE INVENTION

The present invention moves a span of dental floss in a rapid up and down cleaning motion while continuously replacing the span (the word floss in this document is intended to include in its meaning, any of a variety of flexible dental cleaning fibers, tapes, and the like). Specifically, the floss reciprocates vertically in low amplitude oscillations on the tooth surface while constantly changing the floss cleaning surface by simultaneously moving in a transverse direction. The continual horizontal feeding and replacement of floss with a clean dry surface, in concert with the rapid vertical oscillations, loosens the adhering material and carries off the freed particles on and between the floss fibers. This combination of actions is especially important on dental surfaces within the gingival sulci to dislodge deposits and remove the debris. Since the transverse motion of the floss is relatively slow, the only rapid motion is substantially perpendicular to the gingival surfaces. Thus, there is no rapid saw-like motion across soft tissues.

Having a safer and efficient cleaning motion, the tool has the added potential for use as an interdental polisher. In that function, a floss impregnated with a fine abrasive or other polishing material could be used. Hence, the dental hygienist or home user would have a means for interdental polishing heretofore unavailable.

Stationary shield tines are provided which individually enclose moving inner tines that hold the floss span. Thus, the moving tines are shielded to prevent contact with the oral tissues of the user.

Still another safety feature is an adjustable means to allow the floss to slacken if a predetermined amount of force is applied to the cleaning area.

Also included is a means to automatically lock the floss immovably taut when the tool in not running so that the floss can be forced through tight spaces between adjacent teeth.

The tool is loaded with a covered floss supply spool which inhibits floss contamination. Used floss is level-wound on a take-up spool.

The oral portion of the instrument is designed so that the shield tines, as well as the movable inner tines, can be cleaned by simply rinsing under hot running tap water without having to remove parts.

BRIEF DESCRIPTION OF THE DRAWINGS

The accompanying drawings, in combination with the description herewith, illustrate features and advantages of the invention. Like reference characters in different views refer to the same parts. The drawings are intended to illustrate principles of the invention and are not necessarily to scale and in which drawings.

DESCRIPTION OF THE INVENTION

Figure 1:
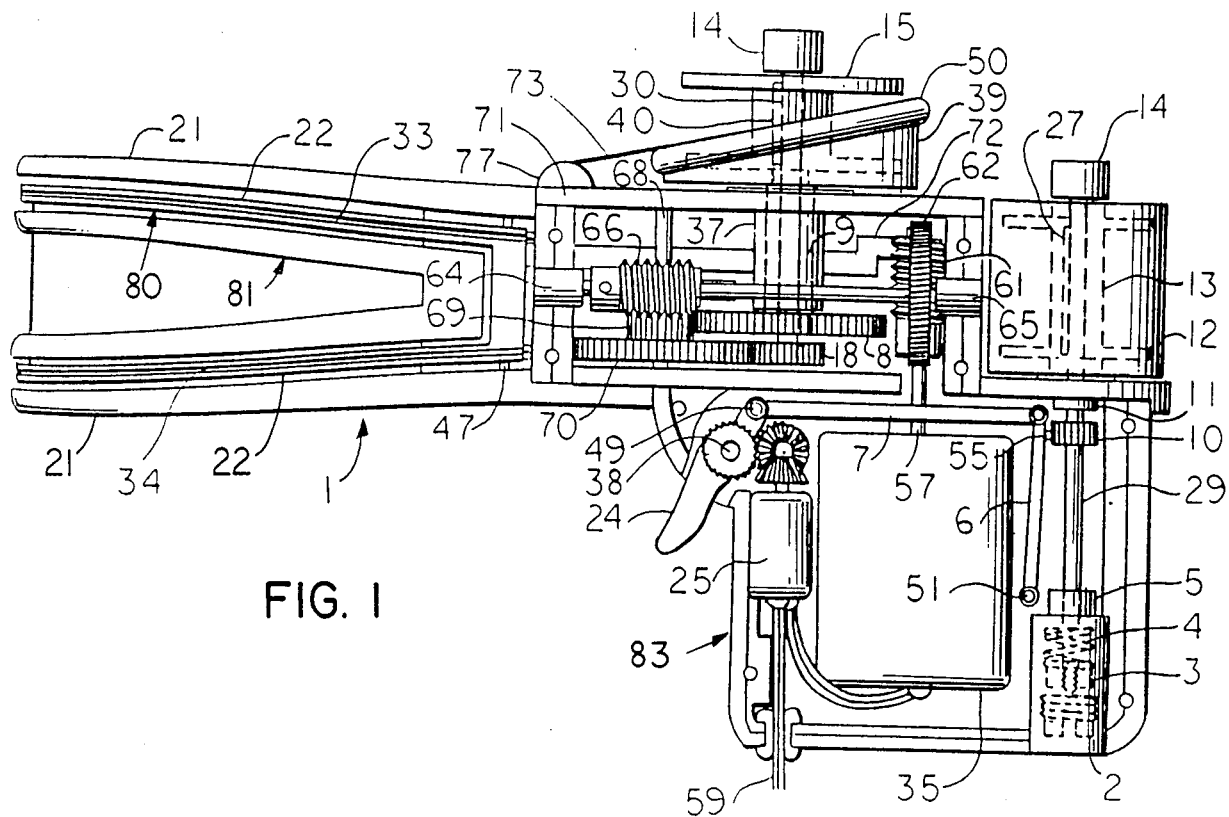
FIG. 1, in a top plan, illustrates the invention with a cover of the gearbox removed and a handgrip cover removed.
Figure 2:
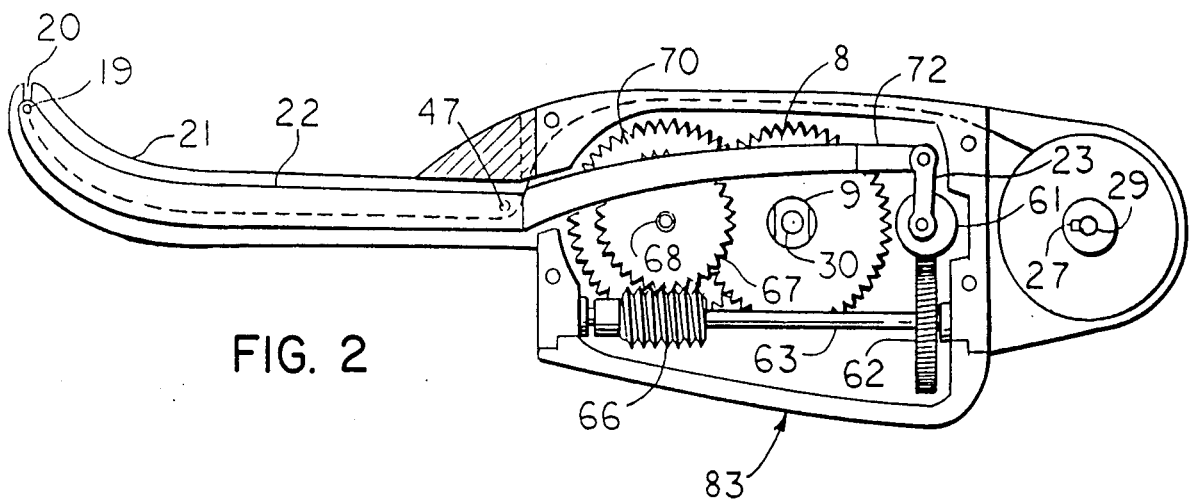
FIG. 2 is a side elevation view of the invention with parts removed which are: the outer half of a shield tine, the take-up spool and its retainer cap, the rail and its support cup, a side cover of the gearbox, and the dispensing spool retainer cap.

The interdental cleaning device 1 described herein and shown in the figures includes two symmetrical forks 80,81; one within the other. In FIG. 1 and 2, each tine 22 of the inner fork 80 is flanked inwardly and outwardly by each half of an outer shield tine 21 in a spaced sandwich arrangement. The inner fork 80 is disposed to reciprocate within the stationary shield fork 81 and though they are in close proximity, they do not contact each other. Extensions of the device housing 83 form the shield tines 21 which are slightly larger than the inner tines 22.

The purpose of the shield fork 81 is to shield the reciprocating inner fork 80 and prevent the latter from contacting the oral tissues of the user. Slots 20 in both halves of each shield tine 21, as shown in FIG. 2, facilitate threading the eyelets 19 of the inner tines 22. This allows passage and motion of floss that spans the inner tines.

Figure 3:
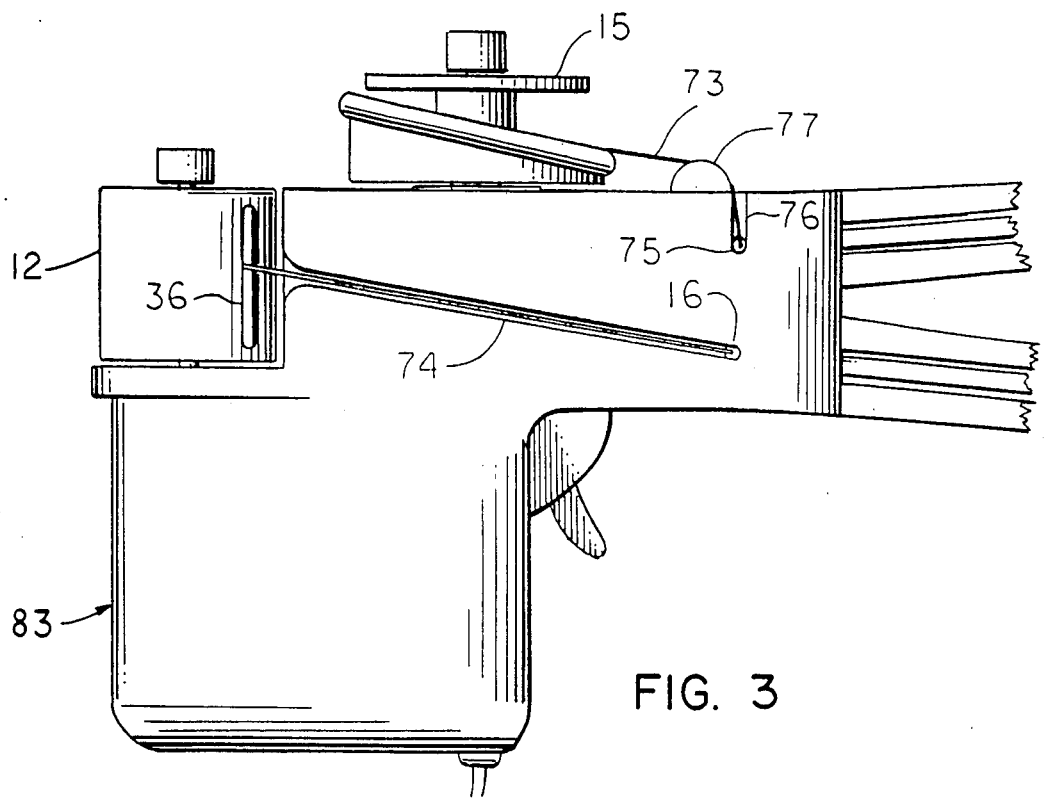
FIG. 3 is a partial bottom view of the invention showing openings and grooves that guide the dental floss.

Shown in the figures is a plastic dispensing spool 13 on which is wound dental floss. A plastic shell 12 covers the dispensing spool to protect the floss from contamination. The spool 13 with its protective shell is mounted on the device by sliding it on a rotatable spindle shaft 29. A flat key 27 projects from the shaft and fits into a keyway in the spool hub to lock them together. The spool 13 is held on shaft 29 by a threaded cap 14. A slot-like opening 36 in the shell wall 12 allows floss to be drawn from the spool as shown in FIG. 3.

A groove 74 in the housing of the device provides a route for the floss to pass from the dispensing spool 13 to an opening 16. After passing through the opening, the floss passes to a groove 33 in a tine 22 of the inner fork (see FIG. 1,2,3 and 5). The floss follows groove 33 which emerges on an outer side of a distal portion of the tine to meet the opening of the eyelet 19. After passing through eyelet 19, the floss spans the fork to pass through the eyelet of the opposite tine to follow a groove 34 back to an opening 75 in the housing. The floss then passes through opening 75 and a guide groove 76, then over a guide 77 to a take-up spool 15. The take-up spool 15 is loaded on a driven shaft 30. A flat key 40 projects from shaft 30 and fits into a keyway in the spool hub to lock them together.

The take-up spool 15 is partially enclosed in a cylindrical cup 39 disposed to rotate about the spool on a common axis. The cup 39 is coaxially fixed to a first bearing 9 in which a journaled portion of shaft 30 is coaxially mounted to rotate. A journaled portion of first bearing 9 is mounted to rotate within a larger second bearing 37. A first gear 18 is coaxially fixed to an end portion of shaft 30 and a second gear 8 is coaxially fixed to an end portion of bearing 9. The cup 39 serves to support an elliptically shaped rail 50 positioned such that its elliptical center is located at the midpoint of the spool core axis. The minor axis of the ellipse is perpendicular to the spool axis. The major axis of the ellipse is tilted at an oblique angle relative to the spool axis. The distance between a pair of lines normal to the spool axis, wherein one line intersects one vertex of the ellipse and the other line intersects the other vertex of the ellipse, is substantially the length of the spool core. Thus, the combination of the rail 50 and support cup 39 form a line traversing cam which partially encloses the spool 15. The elliptical rail is constructed of a material that lends itself to produce low sliding friction (as many plastics and polished metals do) or it is coated with such a material.

The take-up spool 15 is driven by way of the shaft 30 and gear 18 to take up floss 73. The cup 39 and rail 50 are driven, by way of bearing 9 and gear 8, to rotate about spool 15 at a slower rate than the spool rotation rate. The floss 73, drawn over the rotating rail 50, is guided by the angled rail to traverse the core of the spool 15 to become evenly wound thereon.

The preferred number of windings of floss in each successive layer on spool 15 can be obtained by selection of a proper ratio of the rotational rate at which the spool is driven, to the rotational rate at which the elliptical rail 50 is driven. The number of windings per layer is equal to the rotational rate of the spool divided by twice the rotational rate of rail 50.

The take-up spool 15 and rail 50 are driven by an electric motor 35 by way of a speed reduction gear train shown in FIGS. 1 and 2. The gear train drives spool 15 at a slow rotation rate and the rail 50 at a slower rate (preferred rates are determined by standard gear speed formulae). Fixed to the motor shaft 57 is a first worm 61 which rotates a third gear 62. Gear 62 is fixed to a first shaft 63 which is mounted to rotate within bearings 64 and 65. Also fixed to shaft 63 is a second worm 66 which drives a fourth gear 67. The last named gear is fixed to a second shaft 68. A fifth gear 69 and a sixth gear 70 are also mounted and fixed to the second shaft. Shaft 68 is mounted to rotate within two bearings (not shown), one of which is inserted into the gearbox housing and the other is inserted into a gearbox cover 71. When gear 67 is driven by worm 66, gears 69 and 70 drive gears 8 and 18 to rotate the rail 50 and the spool 15, respectively.

Pivotally connected to an end of worm 61 is an end portion of a connecting rod 23 (FIG. 2). The connection is made by way of a pin eccentrically inserted into the worm end; thus, forming an operative crank with the connecting rod. An opposite end portion of connecting rod 23 is pivotally connected to an end portion of a lever 72. The opposite end of the lever is rigidly connected to inner fork 80 as shown in the figures. Thus, the rotation of worm 61 imparts reciprocating motion to the distal end of fork 80 by pivoting the lever and fork about a pivot pin 47. Simultaneously, the worm 61 drives the gear train to level-wind retrieved floss.

The electric motor 35 derives its power from conventional sources such as batteries, a rechargeable power pack, or AC fed through a conductor wire 59. The power is regulated by a rheostat 25. A trigger switch 24 is connected to the control shaft of rheostat 25 by way of the simple gear train indicted in FIG.1. They are situated such that when finger pressure moves the trigger, the control shaft will rotate. Thus, current output of rheostat 25 is controlled by the extent to which the trigger is pressed, thereby controlling the rate at which the motor and the tool operate. Coiled around a trigger pivot pin 38 is a spiral torsion spring (not shown) that spring loads the trigger 24 so that the latter is maintained in a power-off position when released. One end of the spring is attached to the trigger and the other end is attached to the tool housing 83.

Figure 4:
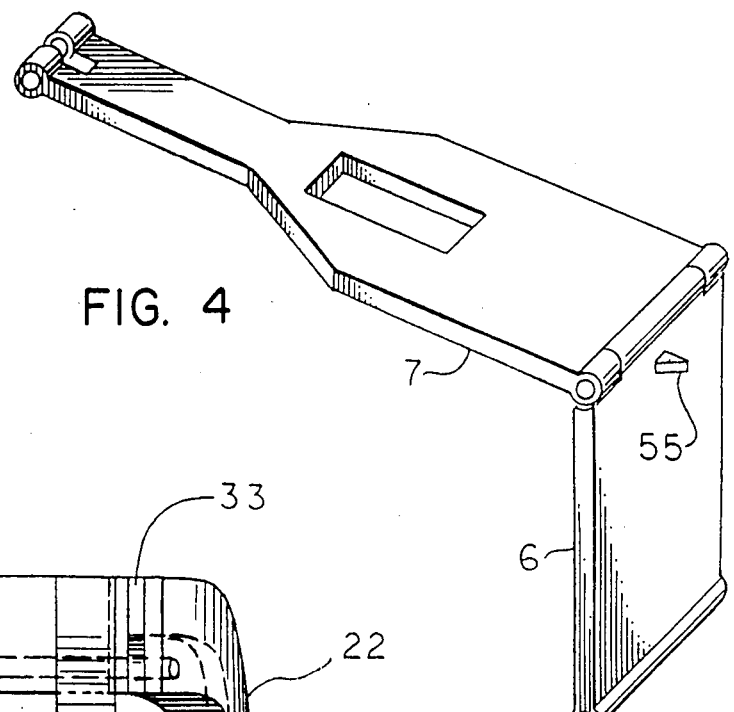
FIG. 4 is an expanded perspective view of the link arm and pawl used in the invention.
Figure 5:
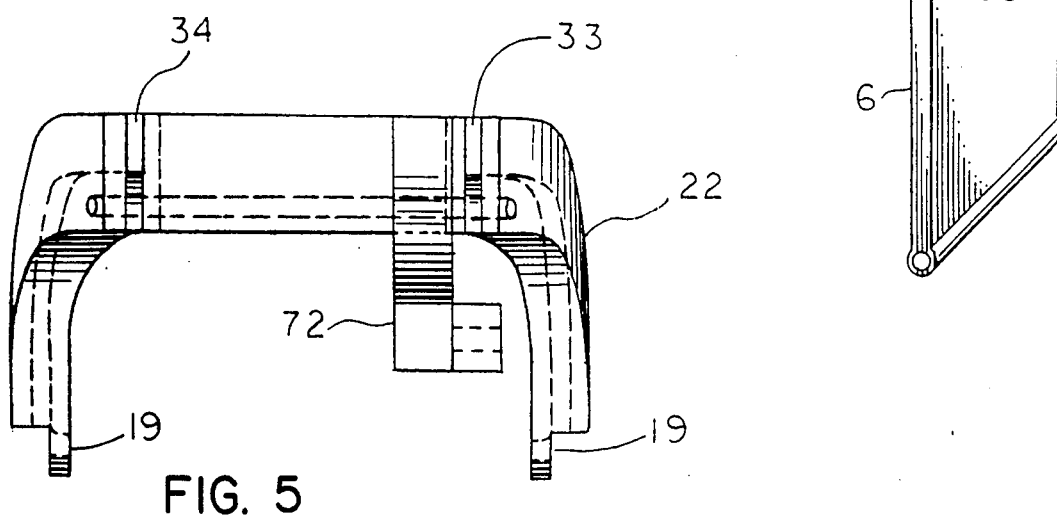
FIG. 5 is an expanded end elevation view of the inner fork used in the invention.

Also slaved to the trigger 24 is a brake system that keeps the dispensing spool immobile while the trigger is not pressed. The brake system comprises a link arm 7, shown in FIGS. 1 and 4, which has one end portion connected to the trigger by way of a movable joint 49. Another movable joint, on an opposite end portion of the link arm 7, connects to one end portion of a pawl 6. An opposite end portion of the pawl 6 is disposed to pivot about a pin 51 which is inserted in the housing 83. An opening in the middle of link arm 7 (FIG. 4) allows the motor shaft 57 to pass through unobstructed.

When trigger 24 is released, current flow stops and the force of the trigger spring presses the pawl 6 against a ratchet wheel 10 which is coaxially fixed to shaft 29. A tooth 55 projecting from pawl 6 engages the wheel 10 and prevents shaft 29 and spool 13 from rotating. Thus, no floss can be drawn from spool 13; a necessary condition which will be explained hereinafter.

An end portion of shaft 29 terminates in a drag assembly. A bearing 5 positioned at an end portion of a cylindrical housing of the drag assembly along with a bearing 11 in housing 83 provide support for the rotatable shaft. The drag assembly comprises a disk 3 coaxially fixed to an end portion of shaft 29. Disk 3 is pressed against a helical spring 4 by an adjustable screw 2. Friction, resulting from the pressure produces the drag effect.

The purpose of the drag is twofold:

(1) To keep the floss taut as it is drawn throughout the tool.

(2) To allow the floss to slacken if the floss segment that spans the inner fork 80 is applied to oral tissues with greater than a predetermined amount of force when operating.

When the tool operates, the floss that spans the inner fork tines 22 moves from one tine to the other. Simultaneously, the floss span reciprocates up and down relative to the teeth. Applied to dental surfaces, the rapid vertical motion in concert with the continually changing floss surface, provided by the slower transverse motion, efficiently loosens and removes deposits. As clean dry floss is continuously fed to the target surface, the freed debris is carried off on and between the used floss fibers.

Since the transverse motion of the floss is slow, the only rapid motion is substantially perpendicular to the gingival surfaces. This safer motion eliminates the need for any rapid saw-like motion across soft tissues. Keeping the drag minimal can also contribute to the safety of the tool.

With a finger on the trigger 24, the user can start, stop, and control the operational speed. The user can draw the floss, that spans the fork 80, into the spaces between his teeth. Where there is resistance, such as at points where there is tight tooth-to-tooth contact, he can urge the floss through with the power off (trigger released). In doing so, the brake associated with the dispensing spool 13 will lock the spool and effectively lock the floss span from moving or slackening. He can then, press the trigger and clean the tooth surfaces. The surfaces can be cleaned down to (or up to for the upper teeth) the attached gingiva. Optionally, a floss impregnated with a polishing material may be used.

When finished, the user can simply rinse the forks under hot tap water. The design of the tines allows the running water to pass between them to rinse their surfaces directly. The tool can be stored with the floss spools in place.

Most of the tool components can be formed from molded plastic. A cheaper embodiment of the tool can be devised by elimination of the floss level-winding feature. This would require elimination of rail 50, support cup 39, first bearing 9, second bearing 37, first gear 18, second gear 8, fourth gear 67, fifth gear 69, sixth gear 70, and second shaft 68 with its bearings. A fixed bearing would replace bearing 9 to receive a journaled portion of shaft 30. Second worm 66 and first shaft 63 would be repositioned to engage a gear coaxially fixed to shaft 30.

It is understood that the preceding description is given merely by way of illustration and not in limitation of the invention and that various modifications may be made thereto without departing from the spirit of the invention as claimed.

I claim:
1. An interdental cleaning tool comprising:
   a housing;
   a pair of reciprocating tines pivotally supported on the housing wherein the tines receive teeth to be cleaned therebetween, each tine having guides for guiding the transfer of dental floss from one tine to the other tine wherein the floss forms a movable span therebetween;
   a dispensing spool having wound dental floss, the spool rotatably supported on the housing for dispensing the dental floss which passes to a reciprocating tine for supplying the span;
   a take-up spool rotatably supported on the housing for retrieving used dental floss passing from a reciprocating tine;
   means for reciprocating the tines up and down relative to the teeth;
   means for producing continuous slow rotation of the take-up spool in order to produce continuous slow longitudinal movement of the floss span; and
   means for separately enclosing each reciprocating tine for shielding the same from contact with oral tissues.

2. The interdental cleaning tool of claim 1, wherein the means for enclosing each reciprocating tine comprises a pair of shield tines which are stationary relative to the housing, each shield tine enclosing the inner and outer sides of one of the reciprocating tines.

3. The interdental cleaning tool of claim 2, wherein each shield tine includes portions defining at least one slot for allowing the floss span to reciprocate therein.

4. The interdental cleaning tool of claim 3, wherein each shield tine includes an elongated opening along its length which allows access to a reciprocating tine for rinsing.

5. An interdental cleaning tool comprising:
   a housing;
   a pair of reciprocating tines pivotally supported on the housing wherein the tines receive teeth to be cleaned therebetween, each tine having guides for guiding the transfer of dental floss from one tine to the other tine wherein the floss forms a movable span therebetween;
   a dispensing spool having wound dental floss, the spool rotatably supported on the housing for dispensing the dental floss which passes to a reciprocating tine for supplying the span;
   a take-up spool rotatably supported on the housing for retrieving used dental floss passing from a reciprocating tine;
   means for reciprocating the tines up and down relative to the teeth;
   means for producing rotation of the take-up spool in order to move the floss span longitudinally; and
   means for locking and unlocking the floss span such that when locked the span is immovably taut so that the same can be forced through tight spaces between adjacent teeth.

6. The interdental cleaning tool of claim 5, wherein the means for locking and unlocking the floss span comprises;
   a ratchet wheel fixedly connected to the dispensing spool;
   a switch mounted to the housing and movable between an ON position and an OFF position; and
   a pawl operatively connected to the switch wherein the pawl engages the ratchet wheel in order to lock the dispensing spool and the floss span when the switch is moved to the OFF position, the pawl disengaging from the ratchet wheel when the switch is moved to the ON position.

7. An interdental cleaning tool comprising:
   a housing;
   a pair of reciprocating tines pivotally supported on the housing wherein the tines receive teeth to be cleaned therebetween, each tine having guides for guiding the transfer of dental floss from one tine to the other tine wherein the floss forms a movable span therebetween;

a dispensing spool having wound dental floss, the spool rotatably supported on the housing for dispensing the dental floss which passes to a reciprocating tine for supplying the span;

means for reciprocating the tines up and down relative to the teeth; and means for drawing floss from the spool if the span is applied to oral tissues with greater than a predetermined amount of force in order to allow the floss span to yieldingly slacken thereby protecting soft tissues.

8. The interdental cleaning tool of claim 7, wherein the means for drawing floss to allow the floss span to slacken if applied with greater than a predetermined amount of force comprises:

a disk fixedly connected to the dispensing spool;

a selectively adjustable screw supported by the housing; and a drag spring positioned between the disk and the screw such that a selective amount of spring drag is imparted on the disk such that the floss span will yieldingly slacken by drawing from the dispersing spool if the span is applied to oral tissues with greater than a predetermined amount of force.

9. An interdental cleaning tool comprising:

a housing;

a pair of reciprocating tines pivotally supported on the housing wherein the tines receive teeth to be cleaned therebetween, each tine having guides for guiding the transfer of dental floss from one tine to the other tine wherein the floss forms a movable span therebetween;

a dispensing spool having wound dental floss, the spool rotatably supported on the housing for dispensing the dental floss which passes to a reciprocating tine for supplying the span;

a take-up spool rotatably supported on the housing for retrieving used dental floss passing from a reciprocating tine;

means for reciprocating the tines up and down relative to the teeth; and means for producing continuous slow rotation of the take-up spool in order to produce continuous slow longitudinal movement of the floss span.

10. The interdental cleaning tool of claim 9, further comprising means for traversing the floss across the take-up spool for level-winding.

11. An interdental cleaning tool comprising:

a housing;

a pair of reciprocating tines supported on the housing wherein the tines receive teeth to be cleaned therebetween;

means for providing a span of dental floss between distal end portions of the tines;

means for reciprocating the tines up and down relative to the teeth; and means for enclosing each reciprocating tine on its inner side in order to prevent the tine from contacting the teeth between the tines during operation of the tool.

12. The interdental cleaning tool of claim 11, wherein the means for enclosing each reciprocating tine comprises a pair of shield tines, each shield tine being divided longitudinally into an inner half and an outer half which are stationary relative to the housing, the inner and outer halves of each shield tine being positioned adjacent respective inner and outer sides of each of the reciprocating tines, respectively.

13. The interdental cleaning tool of claim 12, wherein the inner half of each shield tine includes a portion defining a least one slot shaped and positioned such that the floss span reciprocates up and down therein relative to the teeth.

14. The interdental cleaning tool of claim 13, wherein the outer half of each shield tine includes a portion defining a slot shaped and positioned to facilitate loading the reciprocating tines with floss.

15. The interdental cleaning tool of claim 14, wherein each shield tine is elongated and includes a curved distal end portion for access to remote locations within the oral cavity.

16. An interdental cleaning tool comprising:

a housing;

a pair of reciprocating tines supported on the housing wherein the tines receive teeth to be cleaned therebetween, each tine having guides for guiding the transfer of dental floss from one tine to the other tine wherein the floss forms a span therebetween;

a dispensing spool having wound dental floss, the spool being rotatably supported on the housing for dispensing the dental floss which passes to a reciprocating tine for supplying the span;

a screw supported by the housing such that the position of the screw in the direction of the longitudinal axis of the screw is selectively adjustable by rotation of the same; and resilient means connected to the spool for imposing drag resistance against rotation of the spool, the resilient means being further connected with the screw such that adjustment of the screw results in a change in the amount of drag resistance imposed against rotation of the spool thereby allowing the floss span to slacken if applied with greater than a predetermined amount of force wherein the required amount of force is selectively predetermined by the user.

* * * * *